United States Patent
Nagels

(10) Patent No.: US 10,005,998 B2
(45) Date of Patent: Jun. 26, 2018

(54) BIOENGINEERING AND MEDICAL MODULAR SYSTEM

(71) Applicant: Alpha Plan GmbH, Radeberg (DE)

(72) Inventor: Hans Nagels, Bovenden (DE)

(73) Assignee: Alpha Plan GmbH, Radeberg (DE)

( * ) Notice: Subject to any disclaimer, the term of this patent is extended or adjusted under 35 U.S.C. 154(b) by 313 days.

(21) Appl. No.: 14/370,489

(22) PCT Filed: Jan. 23, 2013

(86) PCT No.: PCT/EP2013/051230
§ 371 (c)(1),
(2) Date: Jul. 3, 2014

(87) PCT Pub. No.: WO2013/110651
PCT Pub. Date: Aug. 1, 2013

(65) Prior Publication Data
US 2014/0342448 A1    Nov. 20, 2014

(30) Foreign Application Priority Data
Jan. 23, 2012    (DE) .................. 10 2012 200 938

(51) Int. Cl.
C12M 3/00    (2006.01)
C12M 1/00    (2006.01)
C12M 1/12    (2006.01)

(52) U.S. Cl.
CPC ............ *C12M 29/04* (2013.01); *C12M 23/42* (2013.01); *C12M 25/10* (2013.01)

(58) Field of Classification Search
CPC .............................. C12M 23/42; C12M 23/44
See application file for complete search history.

(56) References Cited

U.S. PATENT DOCUMENTS 5,202,254 A    4/1993    Amiot et al.
5,597,731 A    1/1997    Young et al.
(Continued)

FOREIGN PATENT DOCUMENTS

CN    101096639 A    1/2008
CN    101622337 A    1/2010
(Continued)

*Primary Examiner* — William H Beisner
(74) *Attorney, Agent, or Firm* — Michael Soderman

(57) ABSTRACT

The invention relates to bioengineering and medical modular systems for the realization of self-contained equipment for influencing biological media, cells, tissue and tissue-like structures as objects.
These modular systems distinguish themselves, in particular, by the fact that the user-specific equipment for influencing the objects can be realized in a simple and economically effective way.
A tub-shaped main body for placement of elements that can be combined with one another is provided for this. Furthermore, at least one container for a liquid medium, a pumping system for a liquid medium, connection elements, filters for the inlet and outlet of gas, at least one filter with a connecting element for a medium, elements for a connection to at least one bioreactor, at least one gas inlet unit or a combination of at least one bioreactor and at least one gas inlet unit are components of the modular system. Moreover, an area for at least one bioreactor, at least one gas inlet unit or a combination with at least one bioreactor and at least one gas inlet unit is available.
Straight pipe sections, bent pipe sections, hose sections, connectors and/or distributors can ideally be connection elements here.

8 Claims, 4 Drawing Sheets

(56) References Cited

U.S. PATENT DOCUMENTS

| | | | |
|---|---|---|---|
| 5,994,129 A * | 11/1999 | Armstrong | C12M 23/42 435/286.1 |
| 6,475,777 B1 | 11/2002 | Sarem et al. | |
| 7,282,362 B2 * | 10/2007 | Pitt | B01L 3/5025 210/321.84 |
| 2002/0055166 A1 | 5/2002 | Cannon et al. | |
| 2008/0213894 A1 | 9/2008 | Antwiler | |
| 2010/0105138 A1 | 4/2010 | Dodd et al. | |
| 2010/0144037 A1 | 6/2010 | Antwiler | |

FOREIGN PATENT DOCUMENTS

| | | |
|---|---|---|
| DE | 4006382 A1 | 3/1991 |
| DE | 4118882 A1 | 12/1992 |
| DE | 69806527 T2 | 9/1998 |
| DE | 10160975 A1 | 6/2003 |
| EP | 0866121 A2 | 9/1998 |
| WO | 2006119622 A1 | 11/2006 |
| WO | 2006122089 A2 | 11/2006 |

\* cited by examiner

BIOENGINEERING AND MEDICAL MODULAR SYSTEM

CROSS REFERENCE TO RELATED APPLICATIONS

This application is the U.S. national stage of International Application No. PCT/EP2013/051230 filed on Jan. 23, 2013, and claims the benefit thereof. The international application claims the benefit under 35 USC 119 of German Application No. 102012200938.8 filed on Jan. 23, 2012; all applications are incorporated by reference herein in their entirety.

BACKGROUND

The invention relates to bioengineering and medical modular systems for the realization of self-contained equipment for influencing biological media, cells, tissue and tissue-like structures as objects.

Bioreactors are known according to their requirements and operating modes.

A bioreactor for carrying out microbial processes on the scale of laboratories and technical colleges and for developing process-adapted, technical bioreactors is known via the document DE 40 06 382 A1. It is comprised of various functional modules and adapters that can be combined with one another for this. The sequence of functional modules and adapters among one another can be arbitrarily chosen.

The document DE 41 18 882 A1 involves a modular system for building bioreactors that can have graduated diameters within a certain range.

The documents are limited to bioreactors.

A rack with at least two cartridges for use in an incubator is known via the document US 2002/0055166. The cartridges are each designed as a housing for a vertical insert. All of the elements of the system are arranged in the housing.

Equipment for influencing biological media, cells or tissues is known from the document U.S. Pat. No. 5,202,254 A. It has a container for a liquid medium, a pumping system for the medium, connecting elements, gas exchange filters and a hollow-fiber bioreactor connected to that. A main body is not described.

SUMMARY

The invention relates to bioengineering and medical modular systems for the realization of self-contained equipment for influencing biological media, cells, tissue and tissue-like structures as objects.

These modular systems distinguish themselves, in particular, by the fact that the user-specific equipment for influencing the objects can be realized in a simple and economically effective way.

A tub-shaped main body for placement of elements that can be combined with one another is provided for this. Furthermore, at least one container for a liquid medium, a pumping system for a liquid medium, connection elements, filters for the inlet and outlet of gas, at least one filter with a connecting element for a medium, elements for a connection to at least one bioreactor, at least one gas inlet unit or a combination of at least one bioreactor and at least one gas inlet unit are components of the modular system. Moreover, an area for at least one bioreactor, at least one gas inlet unit or a combination with at least one bioreactor and at least one gas inlet unit is available.

Straight pipe sections, bent pipe sections, hose sections, connectors and/or distributors can ideally be connection elements here.

DETAILED DESCRIPTION

The invention specified in claim 1 is based on the problem of providing a system of elements in such a way that user-specific facilities for influencing biological media, cells, tissue and tissue-like structures as objects can be realized in a simple and economically effective way.

This problem is solved with the features specified in claim 1.

The medical modular systems for the realization of self-contained equipment for influencing biological media, cells, tissue and tissue-like structures as objects distinguish themselves in particular by the fact that the user-specific equipment for influencing biological media, organisms or parts of organisms can be realized in a simple and economically effective way.

A tub-shaped and horizontally arranged main body for placement of elements that can be combined with one another is provided for this.

Furthermore, at least one container for a liquid medium, at least one pumping system for a liquid medium on a wall or as a component part of a wall of the main body, connection elements, filters for the inlet and outlet of gas, at least one filter with a connecting element for a medium, elements for a connection to at least one bioreactor or at least one gas inlet unit or a combination of at least one bioreactor and at least one gas inlet unit are further components of the modular system. The bioreactor or the gas inlet unit or the combination with at least one bioreactor and at least one gas inlet unit is a further element and is therefore a further component part of the medical modular system.

Moreover, both an area for at least one bioreactor, at least one gas inlet unit or a combination with at least one bioreactor and at least one gas inlet unit and an area for the container for a liquid medium exist that are separated from one another by at least one partition wall.

Straight pipe sections, bent pipe sections, hose sections, connectors and/or distributors can ideally be connection elements here. The distributors will have a T shape or Y shape, for instance. The dimensions are advantageously structured here in such a way that the end areas of the hose sections can simply be pushed onto the other respective connection elements to form a seal. Connections of the individual elements can therefore be realized in a simple way. Further, at least one shuttle valve and/or a check valve can be an element and/or elements.

The tub-shaped main body has at least one partition wall. The spaces for the container with the liquid medium and for the bioreactor or the gas inlet unit or the combination thereof are advantageously separated from one another by the partition wall. Furthermore, the mechanical stability of the main body is increased.

The floors of the spaces and therefore the areas for the container with the liquid medium, on the one hand, and for the bioreactor or the gas inlet unit or the combination thereof, on the other hand, can be designed to be in one plane or in different planes. In the latter case, the tub-shaped main body will have a step in the floor. In a further variant, the floor of the container can be designed to slope in a downwards fashion from the partition wall outwards so that a medium that may leak out of the container will run in the direction of the outer wall opposite the partition wall and accumulate there. The risk that a medium from the container will get into the space with the bioreactor or the gas inlet unit or a combination thereof is therefore further reduced.

The tub-shaped main body can also advantageously have fastening elements for elements of the modular system. This involves, in particular, spaced wall areas; sections of hose pieces can be clamped between the areas as connection elements. Moreover, this involves openings or eyelets for fastening devices.

The pumping system for a liquid medium is arranged in such a way that a drive unit for the pumping system or the energy source for a drive unit coupled to the pumping system can be connected from the outside in a removable fashion. The pumping system and the drive unit are components of a familiar pump. These components are designed to be detachable from one another. Electrical supply lines in the main body are not required for the operation of the pump. The part of the modular system that is to be electrically operated is separated from the equipment for influencing biological media, cells, tissue or tissue-like structures because of that. Devices carrying electrical current are avoided in the main body.

Advantageous design forms of the invention are specified in claims 2 to 8.

According to a further design form, the bioreactor has a housing with a bundle of hollow-fiber membranes opening towards the outside and cap-shaped end pieces. The housing has a pipe section with connectors for the space with the hollow-fiber membranes. The end areas of the hollow-fiber membranes are in bases made of plastic. The end pieces have a connector in each case for the hollow spaces of the hollow-fiber membranes. That is a simple and economically effective realization of the bioreactor. The bundle with the hollow-fiber membranes is placed in the pipe. The hollow-fiber membranes are longer than the pipe section there. Plastic that forms the floors of the housing after it cures is inserted into the end areas of the pipe section with the hollow-fiber membranes. The plastic simultaneously seals up the space surrounding the hollow-fiber membranes and the interior space of the pipe section towards the outside in the process. The projecting hollow-fiber membranes are simply severed after that, so the hollow spaces of the hollow-fiber membranes are accessible from the outside. The end pieces are pushed onto the end areas of the pipe section. The end pieces are designed in such a way that they and the floors form the boundaries of a space in each case. Connectors of the pipe section and the end pieces ensure access to the respective auxiliary resources.

The bundle of hollow-fiber membranes can be designed to have a cross-section that is circular, oval, polygonal, rectangular with rounded-off corners or rectangular with rounded sides.

According to another design form, the bioreactor has a tub-shaped base body with at least one inlet and one outlet in each case in one of the side walls for the medium and in a cover that can be removed from the tub-shaped base body without or with at least one septum. That is a simple and economically effective realization of a bioreactor. Furthermore, a bioreactor of that type can be applied universally; very diverse special add-ons can be placed in the bioreactor. It can therefore be easily constructed in accordance with the objects to be influenced, so a bioreactor of that type can be used in a universal way.

The tub-shaped base body and the cover can be advantageously connected with one another in a tight and detachable way so as to guarantee sterility.

According to an additional design form, the bioreactor has a tub-shaped base body with at least one inlet and one outlet in each case in one of the side walls for the medium, at least one barrier in the tub-shaped base body or as a component part of the tub-shaped base body, a plate-shaped holder with at least one receptacle having a membrane for at least one object in or as a component part of the plate-shaped holder in the tub-shaped base body and a cover that can be removed from the tub-shaped base body with at least one septum.

The inlet and the outlet are arranged in such a way here that the height of the barrier determines the height of the surface of the medium in the tub-shaped base body. Moreover, at least the membrane of the receptacle is located in the medium of the tub-shaped base body.

The floor of the tub-shaped base body can advantageously have a recess arranged so as to correspond with the receptacle so that space for the culture medium exists between the receptacle for at least one object and the recess. Furthermore, the barrier is higher than the plane of the floor with the recess.

The space for the culture medium is consistently limited in the unit because of that. The recess is preferably designed to be a cup for this.

Going further, the floor of the tub-shaped base body can have several recesses arranged so as to correspond with receptacles and the recesses can have connecting channels; in so doing, the barrier will be higher than the channel floors. The space for the culture medium is therefore further limited without the supply of the objects being limited in the receptacles.

The plate-shaped holder can have, moreover, at least one area surrounded by a wall. Aside from one sub-section, this has an opening. The sub-section is arranged to correspond to the septum. The membrane is located in that area. The wall surrounds a space that serves to seat the object. An unambiguous placement of the object in this space is therefore possible. The sub-section advantageously serves as a blocking unit for the device bringing in the object, for instance in the form of a cannula. This prevents the object from being brought into the medium in the base body. The object can therefore be put into the equipment in a simple way.

According to a further design form, the barrier is a partition wall arranged at a distance in front of the outlet in the tub-shaped base body. Furthermore, the inlet and the outlet are arranged in such a way that the height of the partition wall determines the height of the surface of the medium in the tub-shaped base body.

At least one area of the partition wall can be advantageously connected through a predetermined breaking point to the remaining area of the partition wall here so that the height of the medium can thereby be influenced in the base body.

According to another design form, barriers are both a first partition wall arranged at a distance in front of the outlet and a second partition wall arranged at a distance after the inlet in the tub-shaped base body. Furthermore, the inlet and the outlet are arranged in such a way that the height of the partition walls determines the height of the surface of the medium in the tub-shaped base body.

At least one area of at least one of the partition walls can be advantageously connected through a predetermined breaking point to the remaining area of this partition wall here so that the height of the medium can thereby be influenced in the base body.

According to an additional design form, the barrier is an area of the side wall with the outlet of the tub-shaped base body; the distance of the outlet to the floor of the tub-shaped base body is advantageously the height of the barrier, and this distance determines the height of the surface of the medium in the tub-shaped base body.

The floor of the tub-shaped base body according to a further design form has at least one protrusion and/or elevation that influences the flow of the culture medium so that vortices exist in the flow of the medium. The medium is transported through the equipment so that fresh medium is always supplied to the object through the membrane.

According to an additional design form, the gas inlet unit is advantageously an oxygenator.

At least one sensor and/or one device for identifying at least one substance of the medium and/or in the medium is an element according to a further design form. The sensor for this is especially a pH value sensor or an oxygen sensor. The device for identifying a substance is, as an example, an optical device; the composition or individual substances of the medium can be identified via optically detectable changes in the medium. Radiation sources are also known sources for electromagnetic radiation.

According to another design form, the pumping system for the liquid medium is arranged on or in the tub-shaped main body in such a way that the drive unit or the energy source for the drive unit of the pumping system can be connected so as to be removable from the outside. Furthermore, the pumping system can be a component part of the wall of the main body.

The pumping system and the drive unit are components of a familiar pump. These components are designed to be detachable from one another.

The drive unit can be a familiar electric motor for this. The rotor of the electric motor is loosely placed in or with the pumping system. The transfer of motion can conveniently be ensured via a special shape here. In the simplest case, the rotor is flattened in areas or designed to be polygonal in its cross section. The pumping system can have a vane cell, gears, a screw spindle or rotary pistons.

The pumping system can also be a membrane. The membrane can be moved via a drive unit that operates in a mechanical or electromagnetic fashion. In a variant with mechanical excursion, that can take place via an oscillating drive unit, for instance in the form of a piezo drive unit or an eccentric cam coupled to an electric motor. In a variant with excursion brought about in an electromagnetic fashion, the drive unit can be a swinging lever.

Electrical supply lines going into the main body are not required.

According to a further design form, a seating station for the tub-shaped main body is a further component part of the modular system. When placing the tub-shaped main body in the seating station, the drive unit or the energy source for the drive unit is connected to the pumping system.

According to another design form, the drive unit for the pumping system and either the sensor and/or the device for identifying at least one substance of the medium and/or in the medium is connected to a control unit as a component part of the seating station. The control unit can be a familiar data-processing system in the form of a microcontroller. The process for influencing biological media, organisms or parts of organisms as objects can be controlled in accordance with the existing characteristics with appropriate software.

The tub-shaped main body has, according to an additional design form, a rectangular base surface. The pumping system and/or at least one plug-type connector for the sensor and/or a connecting unit of the device for identifying at least one substance of the medium and/or in the medium is located, furthermore, on a wall of the main body or is a component part of this wall. Moreover, the drive unit corresponding to the pumping system and/or at least one plug-type connector corresponding to the plug-type connector for the sensor and/or the counterpart corresponding to the connecting unit of the device for identifying at least one substance of the medium and/or in the medium is arranged in the plane of the seating station. The respective components of the modular system that are to be connected to devices of the seating station are automatically connected when the main body is placed in the seating station. Incorrect connections are avoided by the respective fixed positions of the components of the main body and those of the seating station that are to be connected. Reliable operation of the equipment for influencing biological media, cells, tissue, or tissue-like structures as objects that is realized by the modular system is therefore ensured.

According to another design form, at least the tub-shaped main body, the container, the pumping system, the connection elements, the filters, the bioreactor and the gas inlet unit as component parts of the modular system are advantageously sterile elements of the modular system. They are then simply disposable products.

BRIEF DESCRIPTION OF THE DRAWINGS

An example of the invention is shown in the drawings in the form of its basic structure in each case, and it will be described in more detail below.

The following are shown in the figures.

DETAILED DESCRIPTION OF THE PREFERRED EMBODIMENT

Figure 1:
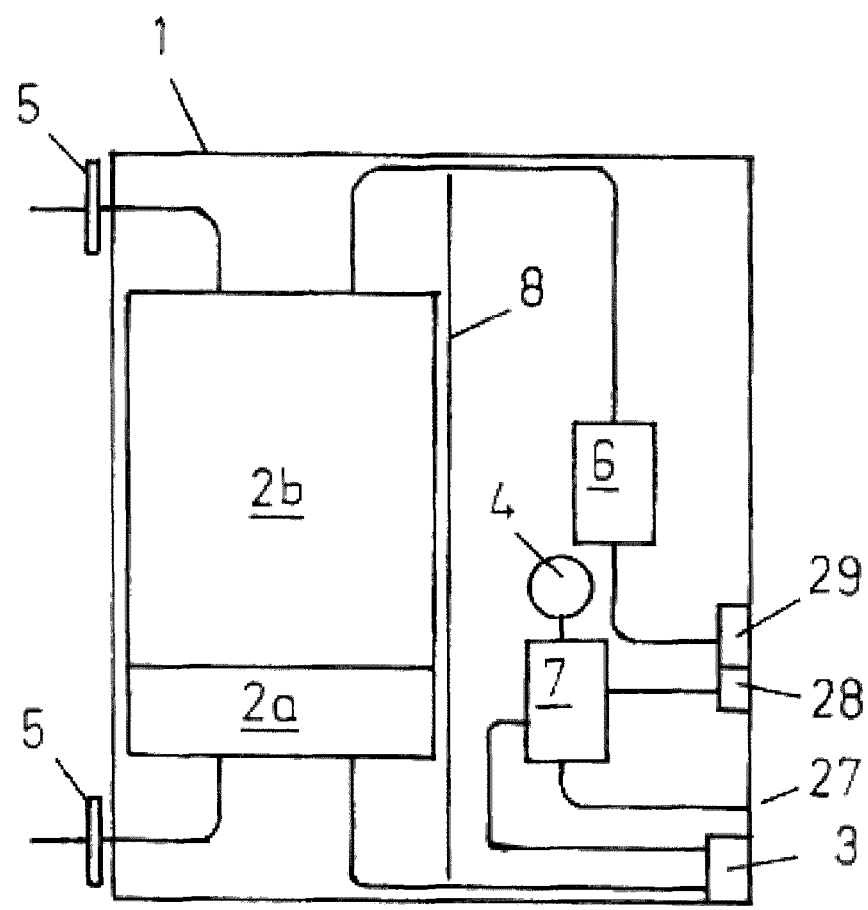
FIG. 1 shows equipment for influencing biological media, cells, tissue and tissue-like structures as objects with a bioreactor and an oxygenator.

A bioengineering and medical modular system for the realization of self-contained equipment for influencing biological media, organisms or parts of organisms as objects is essentially comprised of a tub-shaped main body 1 for placement of elements that can be connected to one another, wherein containers 2 for a liquid medium, a pumping system 3 for a liquid medium, connection elements, filters 4 for the inlet and outlet of gas, filters 5 with a connecting element for a medium, a bioreactor 6 and a gas inlet unit in the form of an oxygenator 7 are elements and therefore component parts of the modular system.

FIG. 1 shows in the form of a basic structure equipment for influencing biological media, cells, tissue and tissue-like structures as objects with a bioreactor and an oxygenator.

The tub-shaped main body 1 has a rectangular base surface and has at least one partition wall 8, so space is available for the containers 2 for the liquid medium and space is available for the bioreactor 6 and the oxygenator 7.

The containers 2 are familiar bags 2 with at least one inflow and outflow unit for the liquid medium in each case. They are arranged one on top of the other; bag 2 with the medium is arranged as the first bag 2a under the bag 2 for used medium as the second bag 2b. At least the first bag 2a is connected to the filter 5 with the connecting element, so it can be filled with medium from the outside.

Figure 2:
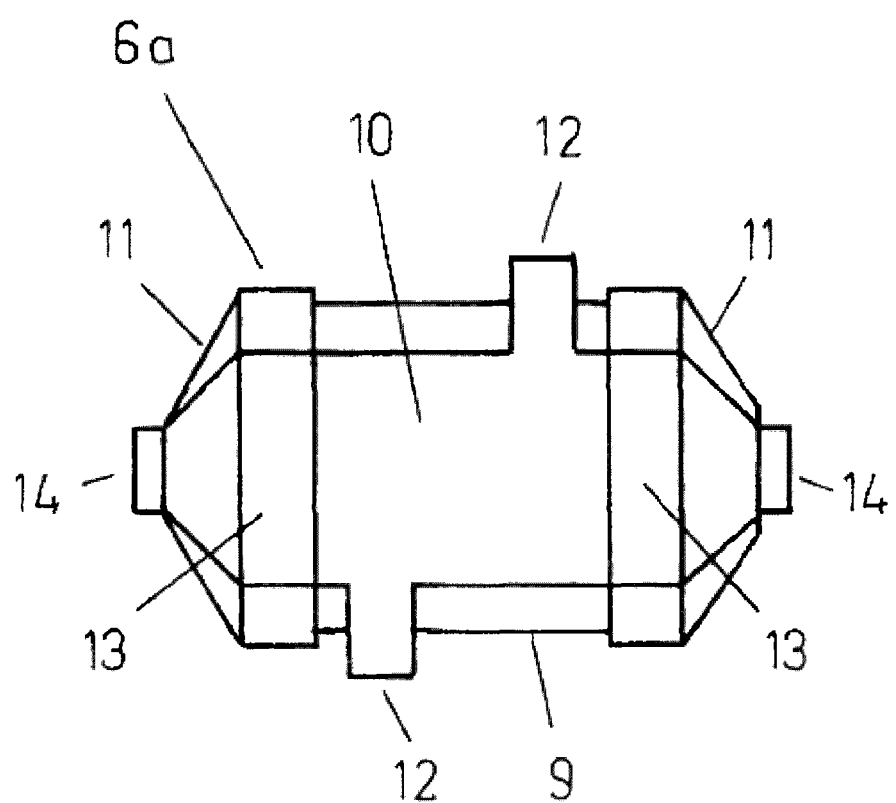
FIG. 2 shows a bioreactor with a bundle of hollow-fiber membranes.

FIG. 2 shows the basic structure of a bioreactor with a bundle of hollow-fiber membranes.

A first bioreactor 6a is comprised of a housing 9 with a bundle 10 of hollow-fiber membranes opening towards the outside and cap-shaped end pieces 11. The housing 9 is a pipe section with connectors 12 for the space with the hollow-fiber membranes. The end areas of the hollow-fiber membranes are in bases 13 made of plastic. The end pieces 11 each have a connector 14 for the hollow areas of the space over the ends of the hollow-fiber membranes including the bases 13 and the hollow-fiber membranes themselves. The bundle 10 of hollow-fiber membranes is designed to be rectangular in its cross section.

A bag 2 with a liquid medium is connected via the pumping system 3 to the oxygenator 7, the bioreactor 6 and the container or a further container 2 for a liquid medium. At least one of the bags 2 is connected to the connecting element of the shell-shaped main body 1 (illustrations of FIGS. 1 and 2).

A second bioreactor 6b for cultivating cells, yeast and bacteria is essentially comprised of a tub-shaped base body 15, a plate-shaped holder 18 and a cover 19.

Figure 3:
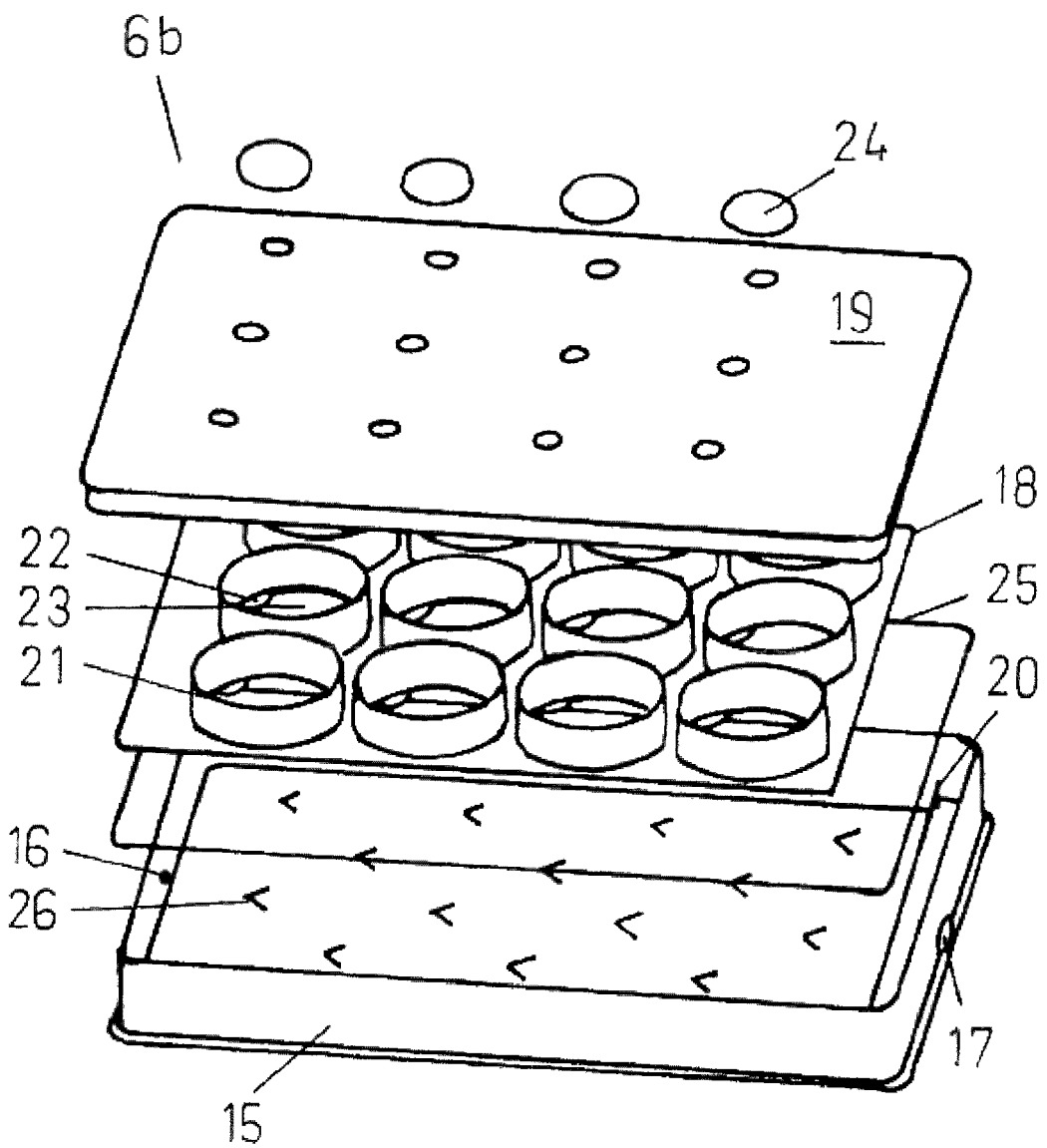
FIG. 3 shows a bioreactor for cultivating cells and tissue cultures, as well as yeast and bacteria in an exploded illustration

FIG. 3 shows the bioreactor 6b for cultivating cells and tissue cultures, as well as yeast and bacteria, in a basic exploded view.

The tub-shaped base body 15 has a rectangular base surface. An inlet 16 and an outlet 17 for the culture medium are located on opposite side walls of the tub-shaped base body 15. A partition wall 20 is arranged at a distance in front of the outlet 17.

The plate-shaped holder 18 is located in the tub-shaped base body 15. It has areas surrounded by walls 21 that each have a through-hole 23 except for a sub-section 22. Furthermore, the membrane that is not shown in FIG. 3 is located in that area. The membranes and the walls 21 therefore represent a receptacle for the object.

The membranes with the receptacles are arranged in the space between the side wall with the inlet 16 and the partition wall 20. The receptacles can, moreover, also be individually placed receptacles or component parts of the plate-shaped holder 18.

The inlet 16 and the outlet 17 are arranged in such a way that the height of the partition wall 20 determines the height of the surface of the culture medium in the tub-shaped base body 15; at least the membranes of the receptacles are located in the culture medium of the tub-shaped base body 15. The inlet 16 and the outlet 17 are arranged to be lower than the height of the partition wall 20 for this.

The cover 19 is equipped with septa 24. The sub-sections 22 are arranged to correspond with the septa 24.

The tub-shaped base body 15 and the cover 19 are tightly connected to one another in a detachable fashion. That is ensured, for instance, via at least one O-ring seal 25 running all the way around between the cover 19 and the tub-shaped base body 15.

The floor of the tub-shaped base body 15 has, in a further embodiment of the second bioreactor 6b, at least one elevation 26 influencing the flow of the culture medium, so vortices exist in the flow of the culture medium.

In a further embodiment of the second bioreactor 6b, the floor of the tub-shaped base body 15 has recesses arranged so as to correspond with the receptacles, so space for the culture medium exists between the receptacles for the objects and the recesses. Furthermore, the floor of the tub-shaped base body 15 has channels that connect the recesses. The partition wall 20 is higher than the plane of the floor with the recesses and higher than the bases of the channels.

At least one area of the partition wall 20 is connected via a predetermined breaking point to the remaining area of the partition wall 20 in a further embodiment of the second bioreactor 6b.

The oxygenator 7 is a receptacle with connectors, so the medium in the container can be enriched with oxygen. The oxygen is supplied from the outside; the tub-shaped main body 1 has a connecting element 27 for this that is connected via a hose piece as the connection element to the oxygenator 7.

According to the illustration in FIG. 1, the first container 2a is connected via the pumping system 3 in the form of a familiar pump 3 and hose pieces as connection elements to the oxygenator 7, the bioreactor 6 and the second bag 2b as the second container 2b. The pumping system 3 is a component part of the wall of the tub-shaped main body 1 for this, or is located in the area with the oxygenator 7 and the bioreactor 6. The drive unit of the pumping system 3 or the energy source for the drive unit of the pumping system 3 can therefore be connected from the outside in a detachable fashion. In the first case, the pump is comprised of the pumping system 3 and the drive unit, which are coupled with one another in a detachable way. The drive unit for this is a familiar electric motor with a rotor that can be connected to the pumping system 3 in a form-locking way. The rotor can be designed to be polygonal or star-shaped in its cross-section for this, at least in parts, or can have at least one flat surface.

Furthermore, a pH value sensor 28 and/or oxygen sensor 29 connected to the oxygenator 7 is arranged on a wall of the tub-shaped main body 1. The latter is optically or electrically coupled outside of the tub-shaped main body 1.

A first oxygen sensor 29 can be located between the oxygenator 7 and the bioreactor 6, and a second oxygen sensor and the pH value sensor 28 can be located after the bioreactor 6.

The main body 1 is advantageously designed for this in such a way that the connectors for the sensor 28, 29 and/or a device for identifying at least one substance of the medium and/or an ion in the medium are arranged on a wall of the main body 1 or are component parts of this wall.

The individual connections are formed by straight pipe sections, bent pipe sections, hose sections, connectors and/or distributors. At the same time, check valves are arranged in such a way that a media flow can also be realized without the bags 2. The reversal of the media flow is realized by either reversing the pumping direction of the pumping system 3 or by integrating an additional pumping system 3 with a reversed flow direction.

The equipment, advantageously, is therefore a horizontal slide-in unit at the same time; the pumping system 3 and at least one sensor make contact when they are put into the intended position and are therefore ready for use. The connecting elements of the tub-shaped main body 1 are freely accessible from the front, so the liquid medium can be supplied in a simple way. The tub-shaped main body 1 advantageously provides protection against leakage of the liquid medium at the same time with an operating mode of the equipment of that type. The liquid medium remains in the tub-shaped main body 1 when there are malfunctions because of leakages. Several sets of equipment of this type can therefore also be arranged one on top of the other in a simple way.

The equipment itself is realized in an economically favorable way, so the equipment can also be disposed of in a simple way after use.

In a further embodiment of the equipment, a seating station 30 for the tub-shaped main body 1 is a component for the modular system.

Figure 4:
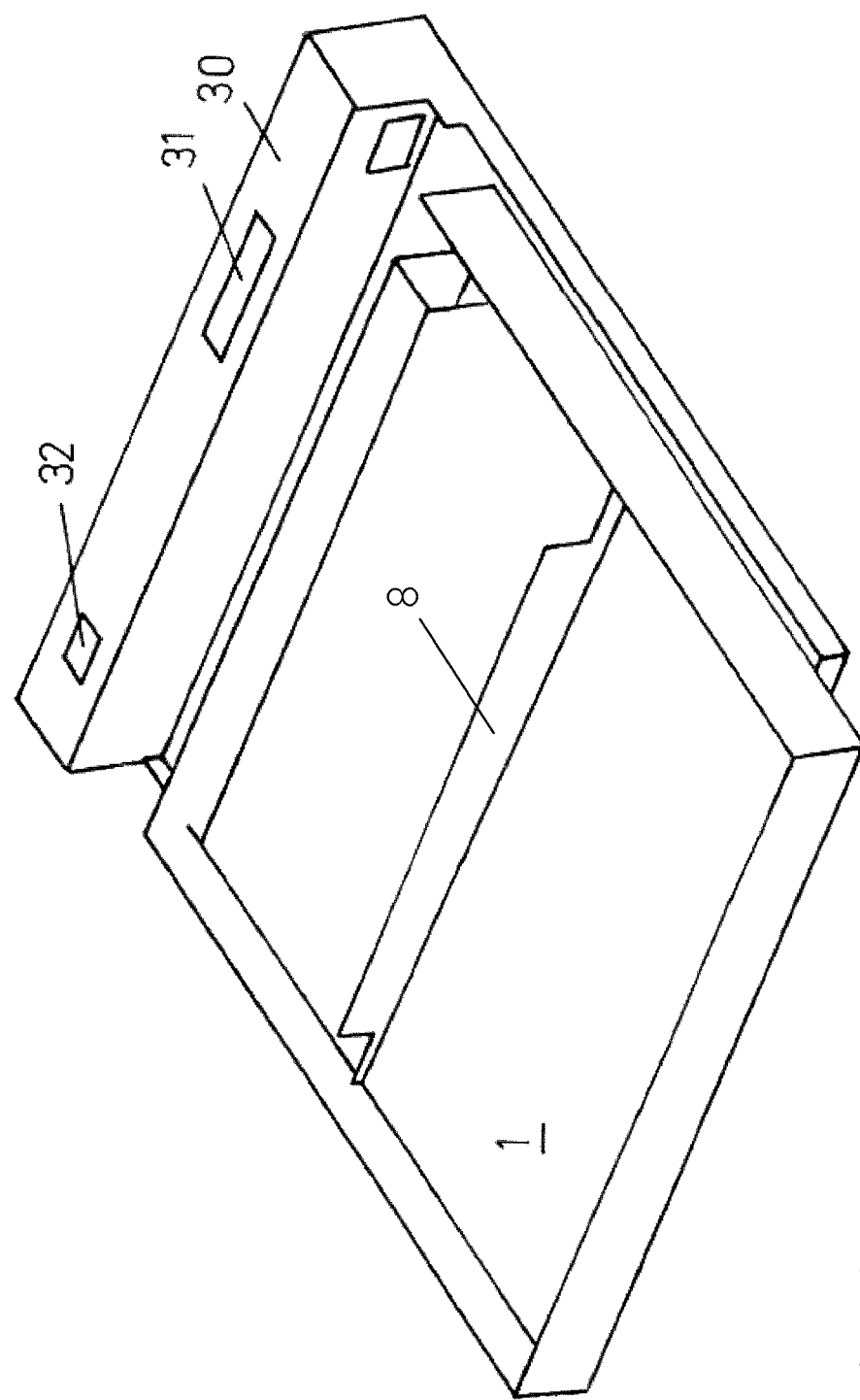
FIG. 4 shows a seating station for equipment for influencing biological media, cells, tissue and tissue-like structures as objects.

FIG. 4 shows the basic structure of a seating station 30 for equipment for influencing biological media, cells, tissue and tissue-like structures as objects.

When placing the tub-shaped main body in the seating station 30, the drive unit and/or the energy source for the drive unit is automatically connected to the pumping system 3 in a detachable way. The seating station 30 has a control unit in the form of a familiar data-processing system as a microcontroller for the drive unit of the pumping system 3 and the signals of the sensors 28, 29. The influencing of biological media, organisms or parts of organisms as objects can therefore be controlled in a targeted way by means of the appropriate software.

The operating state can be presented via a display unit 31 connected to the control unit.

The seating station 30 or several seating stations 30 can be connected to an electrical mains line via an external, detachable power supply unit. An electrical switch 32 is provided for operation.

The invention claimed is:

1. A bioengineering and medical modular system comprising self-contained equipment for influencing biological media, cells, and tissue structures as objects with
   a) a tub-shaped and horizontal main body (1) with
   at least one partition wall separating an area for at least one bioreactor (6) in each case and/or a gas inlet and an area for at least one container (2) for a liquid medium and
   at least one pumping system (3) for the liquid medium on a wall on or in the tub-shaped and horizontal main body (1) or as a component part of a wall of the tub-shaped and horizontal main body (1),
   so that a drive unit or an energy source for the drive unit of the pumping system (3) can be connected from the outside in a detachable manner,
   for placement of elements for the realization of the self-contained equipment,
   comprising
      at least one sensor (28, 29) and/or device for identifying at least one substance of the liquid medium and/or in the liquid medium,
      the container (2) for the liquid medium,
      at least one filter (5) with a supply connector for the liquid medium,
      couplings comprising straight pipe sections, bent pipe sections, hose sections, connectors and/or distributors in a T or Y shape, wherein the end areas of the hose sections can be pushed onto the other respective couplings to form a seal,
      an oxygenator (7) as a gas inlet,
      filters (4) for an inlet and outlet of gas,
   and
      the bioreactor (6),
   so that the container (2) with the liquid medium is connected via the pumping system (3) to the oxygenator (7), the bioreactor and the container (2) or a further container for the liquid medium,
   and wherein
   the bioreactor (6) has a housing (9) with a bundle (10) of hollow-fiber membranes opening towards the outside and cap-shaped end pieces (11), the housing (9) is a pipe section with connectors (12) for the space with the hollow-fiber membranes, end areas of the hollow-fiber membranes are in bases (13) made of plastic and the end pieces (11) each have connectors (14) for hollow spaces of the hollow-fiber membranes,
   and
   b) a seating station (30) for the tub-shaped and horizontal main body (1) with a controller, wherein, when the tub-shaped and horizontal main body (1) is placed in the seating station (30), the drive unit or the energy source for the drive unit is connected to the pumping system (3), on the one hand, and, on the other hand, the drive unit and either the sensor (28, 29) and/or the device for identifying at least one substance of the liquid medium and/or in the liquid medium are connected to the controller,
   the tub-shaped and horizontal main body (1) has a rectangular base surface,
   the pumping system (3) and/or at least one plug-type connector for the sensor (28, 29) and/or a coupling of the device for identifying at least one substance of the liquid medium and/or in the liquid medium is located on a wall of the tub-shaped and horizontal main body (1) and
   the drive unit corresponding to the pumping system (3) and/or at least one plug-type connector corresponding to the plug-type connector for the sensor (28, 29) and/or the counterpart corresponding to the coupling of the device for identifying at least one substance of the liquid medium and/or in the liquid medium is arranged in a plane of the seating station (30).

2. The modular system according to claim 1, wherein at least the tub-shaped and horizontal main body (1), the container (2), the pumping system (3), the couplings, the filters (4, 5), the bioreactor (6) and the gas inlet, as component parts of the modular system, are sterile elements of the modular system.

3. A bioengineering and medical modular system comprising self-contained equipment for influencing biological media, cells, and tissue structures as objects with
   a) a tub-shaped and horizontal main body (1) with
   at least one partition wall separating an area for at least one bioreactor (6) in each case and/or a gas inlet and an area for at least one container (2) for a liquid medium and
   at least one pumping system (3) for the liquid medium on a wall on or in the tub-shaped and horizontal main body (1) or as a component part of a wall of the tub-shaped and horizontal main body (1),
   so that a drive unit or an energy source for the drive unit of the pumping system (3) can be connected from the outside in a detachable manner,
   for placement of elements for the realization of the self-contained equipment,
   comprising
      at least one sensor (28, 29) and/or device for identifying at least one substance of the liquid medium and/or in the liquid medium,
      the container (2) for the liquid medium,
      at least one filter (5) with a supply connector for the liquid medium,
      couplings comprising straight pipe sections, bent pipe sections, hose sections, connectors and/or distributors in a T or Y shape, wherein the end areas of the hose sections can be pushed onto the other respective couplings to form a seal,
      an oxygenator (7) as a gas inlet, filters (4) for an inlet and outlet of gas,
and
the bioreactor (6),
so that the container (2) with the liquid medium is connected via the pumping system (3) to the oxygenator (7), the bioreactor and the container (2) or a further container for the liquid medium
and wherein
the bioreactor (6) has a tub-shaped base body (15) with at least one inlet (16) in each case and an outlet (17) in one of the side walls for the liquid medium and a cover (19) with or without at least one septum (24), said cover being capable of being removed from the tub-shaped base body (15),
and
b) a seating station (30) for the tub-shaped and horizontal main body (1) with a controller, wherein, when the tub-shaped and horizontal main body (1) is placed in the seating station (30), the drive unit or the energy source for the drive unit is connected to the pumping system (3), on the one hand, and, on the other hand, the drive unit and either the sensor (28, 29) and/or the device for identifying at least one substance of the liquid medium and/or in the liquid medium are connected to the controller,
the tub-shaped and horizontal main body (1) has a rectangular base surface,
the pumping system (3) and/or at least one plug-type connector for the sensor (28, 29) and/or a coupling of the device for identifying at least one substance of the liquid medium and/or in the liquid medium is located on a wall of the tub-shaped and horizontal main body (1) and
the drive unit corresponding to the pumping system (3) and/or at least one plug-type connector corresponding to the plug-type connector for the sensor (28, 29) and/or the counterpart corresponding to the coupling of the device for identifying at least one substance of the liquid medium and/or in the liquid medium is arranged in a plane of the seating station (30).

4. A bioengineering and medical modular system comprising self-contained equipment for influencing biological media, cells, and tissue structures as objects with
a) a tub-shaped and horizontal main body (1) with
at least one partition wall separating an area for at least one bioreactor (6) in each case and/or a gas inlet and an area for at least one container (2) for a liquid medium and
at least one pumping system (3) for the liquid medium on a wall on or in the tub-shaped and horizontal main body (1) or as a component part of a wall of the tub-shaped and horizontal main body (1),
so that a drive unit or an energy source for the drive unit of the pumping system (3) can be connected from the outside in a detachable manner,
for placement of elements for the realization of the self-contained equipment,
comprising
at least one sensor (28, 29) and/or device for identifying at least one substance of the liquid medium and/or in the liquid medium,
the container (2) for the liquid medium,
at least one filter (5) with a supply connector for the liquid medium,
couplings comprising straight pipe sections, bent pipe sections, hose sections, connectors and/or distributors in a T or Y shape, wherein the end areas of the hose sections can be pushed onto the other respective couplings to form a seal,
an oxygenator (7) as a gas inlet,
filters (4) for an inlet and outlet of gas,
and
the bioreactor (6),
so that the container (2) with the liquid medium is connected via the pumping system (3) to the oxygenator (7), the bioreactor and the container (2) or a further container for the liquid medium,
and wherein
the bioreactor (6) has a tub-shaped base body (15) with at least one inlet (16) in each case and an outlet (17) in one of the side walls for the liquid medium, at least one barrier in the tub-shaped base body (15) or as a component part of the tub-shaped base body (15), a plate-shaped holder (18) with at least one receptacle having a membrane for the at least one object in or as a component part of the plate-shaped holder (18) in the tub-shaped base body (15), and a cover (19) with at least one septum (24), said cover being capable of being removed from the tub-shaped base body (15), wherein the inlet (16) and the outlet (17) are arranged in such a way that the height of the barrier determines the height of the surface of the liquid medium in the tub-shaped base body (15) and wherein at least the membrane of the receptacle is located in the liquid medium of the tub-shaped base body (15),
and
b) a seating station (30) for the tub-shaped and horizontal main body (1) with a controller, wherein, when the tub-shaped and horizontal main body (1) is placed in the seating station (30), the drive unit or the energy source for the drive unit is connected to the pumping system (3), on the one hand, and, on the other hand, the drive unit and either the sensor (28, 29) and/or the device for identifying at least one substance of the liquid medium and/or in the liquid medium are connected to the controller,
the tub-shaped and horizontal main body (1) has a rectangular base surface,
the pumping system (3) and/or at least one plug-type connector for the sensor (28, 29) and/or a coupling of the device for identifying at least one substance of the liquid medium and/or in the liquid medium is located on a wall of the tub-shaped and horizontal main body (1) and
the drive unit corresponding to the pumping system (3) and/or at least one plug-type connector corresponding to the plug-type connector for the sensor (28, 29) and/or the counterpart corresponding to the coupling of the device for identifying at least one substance of the liquid medium and/or in the liquid medium is arranged in a plane of the seating station (30).

5. The modular system according to claim 4, wherein the barrier is a partition wall (20) arranged at a distance in front of the outlet (17) in the tub-shaped base body (15) and that the inlet (16) and the outlet (17) are arranged in such a way that the height of the partition wall (20) determines the height of the surface of the liquid medium in the tub-shaped base body (15).

6. The modular system according to claim 4, wherein both a first partition wall (20) arranged at a distance in front of the outlet (17) and a second partition wall (20) arranged at a distance after the inlet are barriers in the tub-shaped base body (15) and that the inlet (16) and the outlet (17) are arranged in such a way that the height of the petition walls (20) determines the height of the surface of the medium in the tub-shaped base body (15).

7. The modular system according to claim 4, wherein the barrier is an area of a side wall with the outlet (17) of the tub-shaped base body (15), wherein the distance of the outlet (17) to the floor of the tub-shaped base body (15) is the height of the barrier and this distance determines the height of the surface of the medium in the tub-shaped base body (15).

8. The modular system according to claim 4, wherein the floor of the tub-shaped base body (15) has at least one protrusion and/or elevation (26) influencing the flow of a culture medium so that vortices exist in the flow of the culture medium.

* * * * *